(12) United States Patent
Patten

(10) Patent No.: US 7,418,867 B2
(45) Date of Patent: Sep. 2, 2008

(54) REMOTE USE OF ULTRASONIC SENSORS

(76) Inventor: Eric Russell Patten, 507 Green Ridge, Longview, TX (US) 75605

( * ) Notice: Subject to any disclaimer, the term of this patent is extended or adjusted under 35 U.S.C. 154(b) by 296 days.

(21) Appl. No.: 10/856,552

(22) Filed: May 27, 2004

(65) Prior Publication Data

US 2005/0262945 A1    Dec. 1, 2005

(51) Int. Cl.
*G01N 29/00* (2006.01)
(52) U.S. Cl. .............. 73/627; 73/599; 73/600; 73/644
(58) Field of Classification Search ............ 73/627, 73/599, 600, 602, 644, 641, 628, 629
See application file for complete search history.

(56) References Cited

U.S. PATENT DOCUMENTS

| 4,022,055 A | * | 5/1977 | Flournoy et al. .......... 73/627 |
| 4,462,256 A | * | 7/1984 | Moffett ............... 73/642 |
| 4,470,304 A | * | 9/1984 | Nusbickel et al. ......... 73/611 |
| 4,524,621 A | * | 6/1985 | Yamanaka ............ 73/597 |
| 5,251,487 A | * | 10/1993 | Marshall ............... 73/644 |
| 5,894,092 A | * | 4/1999 | Lindgren et al. ......... 73/598 |
| 5,974,889 A | * | 11/1999 | Trantow ............... 73/624 |
| 5,987,991 A | * | 11/1999 | Trantow et al. .......... 73/624 |
| 6,763,698 B2 | * | 7/2004 | Greenwood ............ 73/30.01 |

* cited by examiner

*Primary Examiner*—Hezron E. Williams
*Assistant Examiner*—Jacques M. Saint-Surin

(57) ABSTRACT

A method and apparatus for conducting ultrasonic inspections of what would normally be inaccessible areas of objects for such properties as thickness, cracks, discontinuities, density, pits and holes. In addition, a method and apparatus for improving ultrasonic inspections with a method for removing trapped gasses from the couplant. Also, a method and apparatus for conduction ultrasonic inspections of objects for multiple properties such as thickness, cracks, discontinuities density, pits and holes with at the same time with a single transducer. Further more, a method and apparatus for conducting rapid ultrasonic inspections of concave surfaces of objects for multiple properties such as thickness, cracks, discontinuities density, pits and holes with a single transducer. This invention allows for the inspection of the entire surface of the object or specific defined areas.

4 Claims, 5 Drawing Sheets

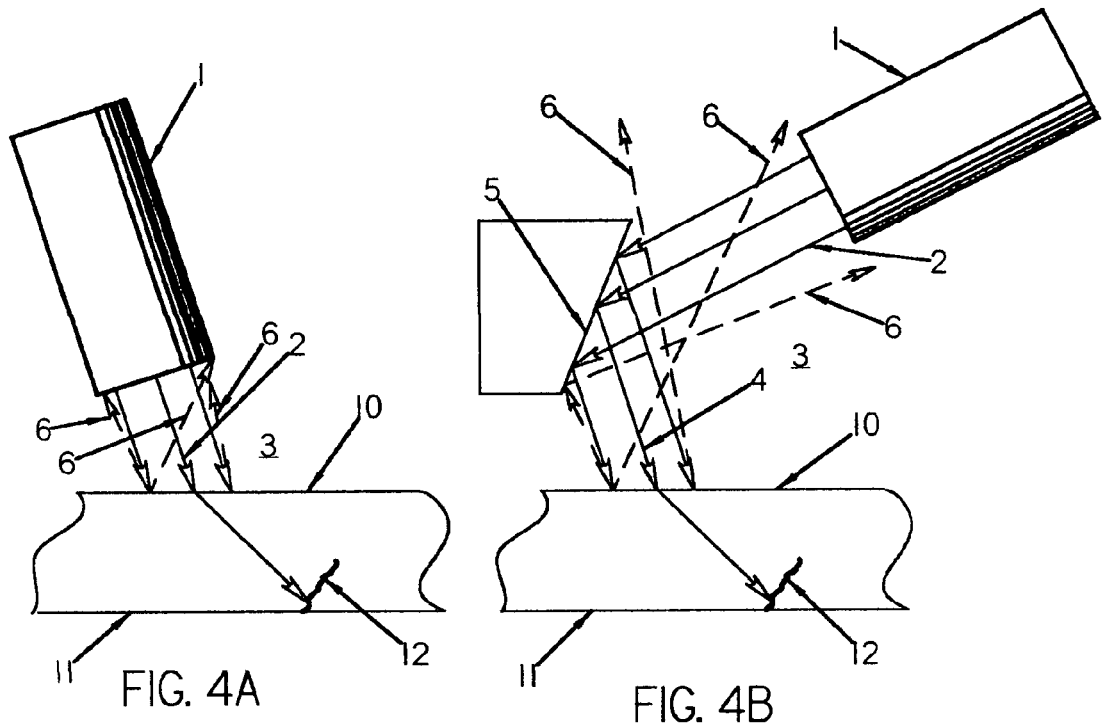
FIG. 4A
FIG. 4B
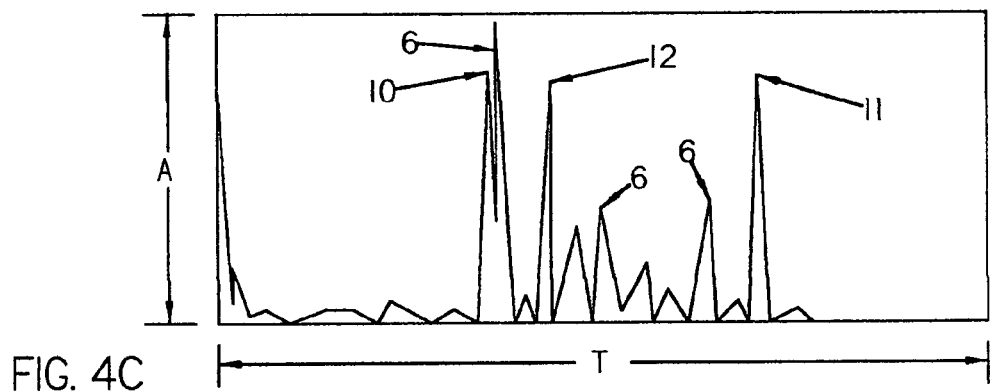
FIG. 4C
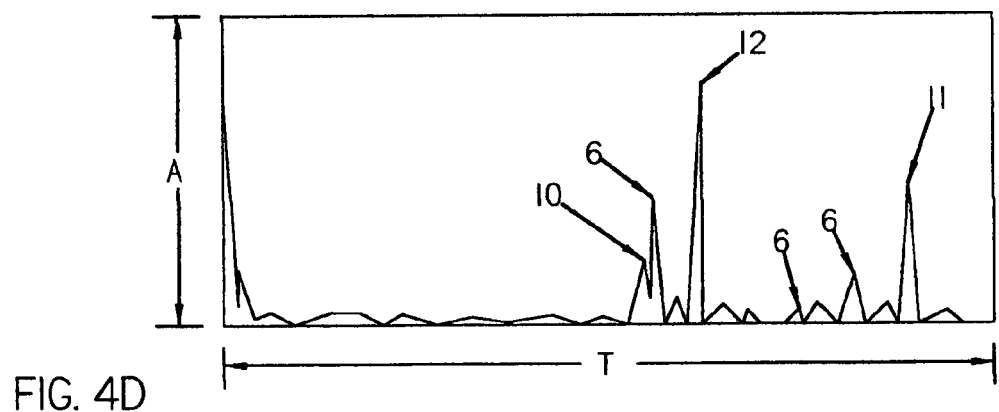
FIG. 4D

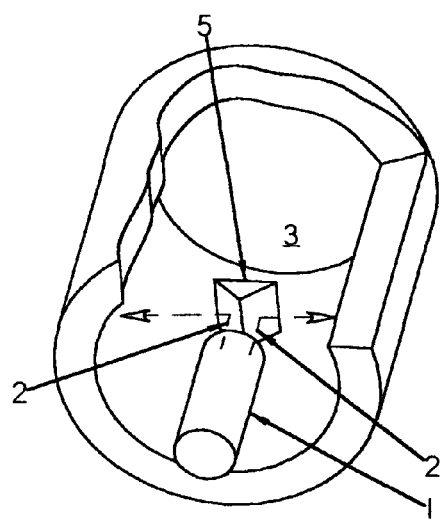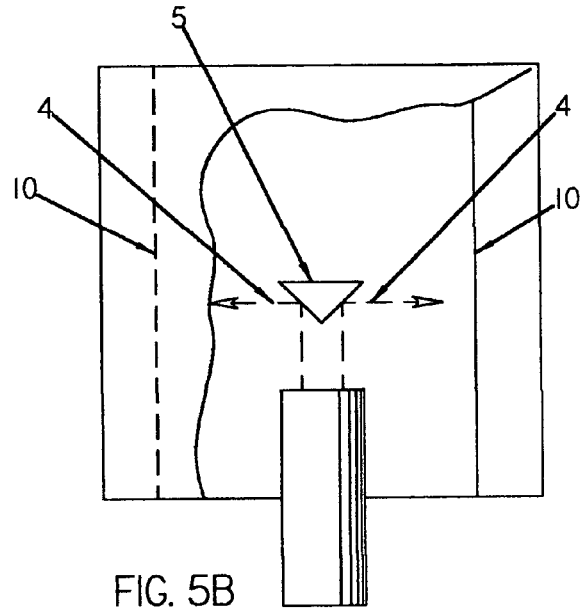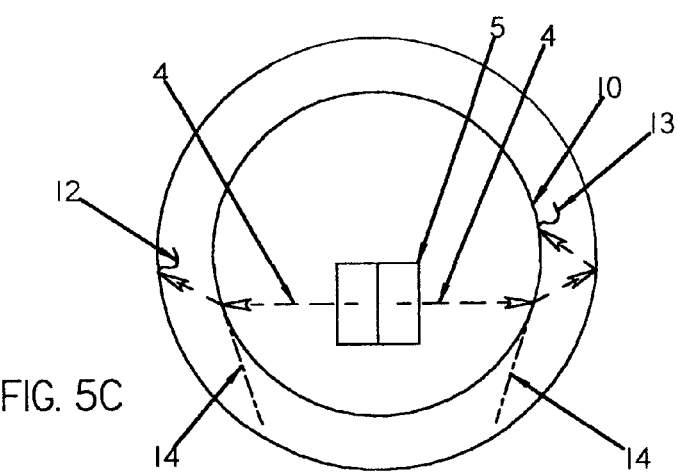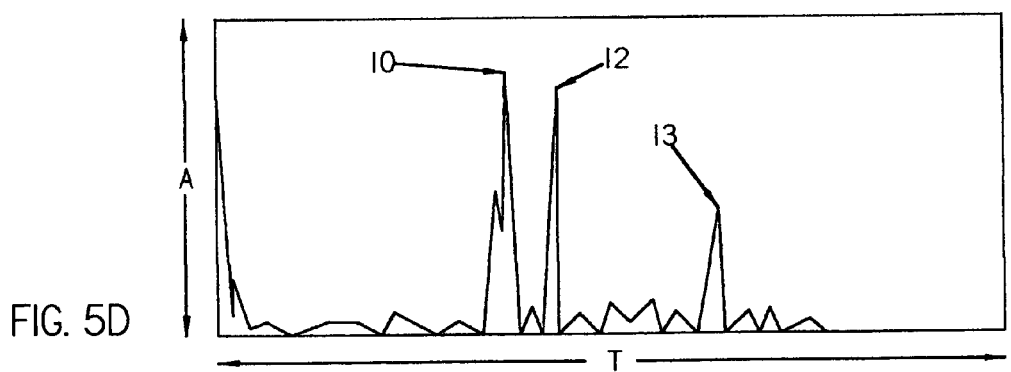
FIG. 5A
FIG. 5B
FIG. 5C
FIG. 5D

REMOTE USE OF ULTRASONIC SENSORS

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISK

Not Applicable

BACKGROUND OF THE INVENTION

Field of the Invention

Ultrasonic sound waves are used to investigate objects for such properties as thickness, the presence of cracks, discontinuities (commonly known as flaws), density, pits and holes, by transmitting sound pulses from an acoustic transmitter, through a couplant, usually water, that conveys the sound from the transmitter to the object, and measuring the reflected sound waves, or echoes, from the surfaces, cracks, discontinuities, density, pits and holes. These echoes are then analyzed to determine what properties caused them. This is normally done using either one Ultrasonic transducer that generates the sound pulse and then measures the echoes that return along the same path, or two transducers, one that generates the sound pulse, and a second that measures the echo for each area to be inspected. The two transducer system can have both transducers contained in the same housing, or separately mounted. These ultrasonic techniques for measuring the properties of objects are well documented and common in industry and need not be described in great detail in this document. Often these ultrasonic tests are made difficult or impossible by obstructions, restricted space, restricted access, or test equipment that is larger than the area to be inspected, which limits the size of the area to be inspected. Also, ultrasonic waves are attenuated by air, so any air trapped in the couplant with significantly weaken the returning signal, and can invalidate the test. In addition, ultrasonic inspections for discontinuities require multiple transducers aligned along alternate axis to inspect any specific area, due to the fact that, if the discontinuity is in line with, or along the same axis as the sound path, the sound will pass the discontinuity without reflecting, and therefore not be detected.

These tests can also be made more difficult by spurious signals, commonly known as noise caused by the sound pulses echoing from unfavorable surface conditions, minor material defects, couplant turbulence or particles in the couplant.

This invention provides a means to avoid these problems without compromising the ultrasonic test.

Ultrasonic sound waves can be either transmitted along the surface of an object, into an object, be reflected from the surface of that object, or a combination of all three, depending on the angle between the direction the sound wave is traveling and the surface of the material, and the condition of the surface. The critical angle of refraction is the angle between the sound wave direction and the normal to the surface below which the majority of the sound will be transmitted into the object, and above which it will be reflected (approximately 18° for steel). At this angle, the sound pulses are transferred to the surface of the object, and very little of the energy is reflected, or enters the object.

If the angle between the direction of the sound pulse and the normal to the object surface is greater than the critical angle, nearly all of the sound pulse is reflected. This phenomena can be used to redirect the sound pulses of an Ultrasonic inspection system to avoid obstacles, inspect in confined spaces, orient the transducers, split the pulse into multiple signals, manipulate the sound pulses to inspect objects or portions of objects that otherwise would be difficult or impossible to inspect, and reduce the noise detected by the transducer.

The following U.S. patents use reflected signals for Ultrasonic Inspection, but do not address the problems addressed in this patent.

U.S. Pat. No. 4,361,044 Kupperman
    This patent discloses a method to inspect the inside of cylindrical holes with two rotating mirrors U.S. Pat. No. 4,022,055 Flournoy et al.
    This patent discloses a method to inspect the inside of cylindrical holes with any number of transducers each reflecting from split mirrors that separate the Ultrasonic pulse into two signals, one for thickness and one for transverse flaw U.S. Pat. No. 4,008,603 Paulissen
    This patent discloses a method to inspect the inside of cylindrical holes with one rotating mirror U.S. Pat. No. 3,550,438 Kapluszak
    This patent discloses a method to inspect hot objects with one mirror that focuses the ultrasonic pulse U.S. Pat. No. 3,028,752 Bacon
    This patent discloses a method to focus the Ultrasonic pulse with a reflector

BRIEF SUMMARY OF THE INVENTION

It is the object of this invention to provide a means, through the use of reflectors to orient the ultrasonic pulse to:
1. Ultrasonically inspect areas of objects in restricted areas
2. Facilitate the purging of air from the couplant
3. Reduce the spurious, unwanted reflections commonly known as noise
4. Split the ultrasonic pulse into multiple parts to analyze multiple flaw signals with one transducer

BRIEF DESCRIPTION OF SEVERAL VIEWS OF THE DRAWINGS

The various advantages and novel features of this invention will be more fully understood when the accompanying descriptions are read in conjunction with accompanying drawings in which like reference numbers refer to like parts, and in which:

FIG. 4A is a side view demonstrating a transducer inspecting a horizontal surface of thickness collecting spurious signals (noise).

FIG. 4B is the same inspection represented in FIG. 4A using a reflector to reduce the noise.

FIG. 4C is an oscillograph which shows various echo pulse signals which are the reflected pulses that are returned from the surfaces of an object being measured in the manner indicated by FIG. 4A.

FIG. 4D is an oscillograph which shows various echo pulse signals which are the reflected pulses that are returned from the surfaces of an object being measured in the manner indicated by FIG. 4B.

FIGS. 5A, 5B and 5C are respectively an isometric cut away view, a top cut-away view and an end view demonstrating a transducer inspecting a curved surface for multiple discontinuities parallel to the axis of the curve using a reflector to split the sound pulses.

FIG. 5D is an oscillograph which shows various echo pulse signals which are the reflected pulses that are returned from the surfaces of a wall being measured in the manner indicated by FIG. 5A.

DETAILED DESCRIPTION OF THE INVENTION

The use of ultrasonic sound waves to investigate objects for such properties as thickness, the presence of cracks, discontinuities (flaws), density, pits and holes is commonly employed in industry. However, in using this technique many areas of objects of interest that would be inspected ultrasonically could not be due to obstructions, overhangs, space constraints and physical geometries that limited the accessibility to those areas with an ultrasonic transducer. This invention provides a method to inspect areas with limited accessibility through the use of reflected sound waves. It will be understood that all descriptions in this document assumes that area between the transducers and objects to be inspected is filled with a fluid which will act as a good conductor for acoustic energy (couplant). Thickness and discontinuities are used as examples for this discussion, but it is understood that the same principles apply to all properties that can be detected or analyzed with ultrasonic pulses.

This invention also provides a method to inspect multiple areas with limited accessibility through the use of a reflector to separate or split the ultrasonic sound pulses into multiple segments and evaluate multiple individual areas of an object with single transducers. Each of these segments is referred to as a "direction" in industry and it should be noted that the number of directions that can be inspected with a single transducer with this invention is only limited by the electronics or the operator used to interpret the returned sound pulses and is therefore not limited to the examples illustrated here in FIGS. 5, 6 and 7.

Figure 1A:
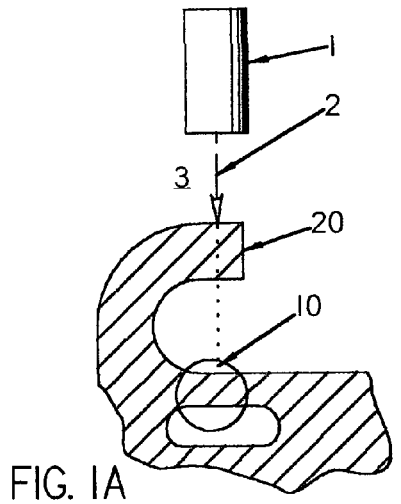
FIG. 1A is a side view demonstrating an attempt to inspect an area for thickness inside a restricted space with an ultrasonic transducer.

FIG. 1A shows a cross sectional side view of an attempt to measure the thickness of the material of an area 10 by transmitting an ultrasonic pulse along path 2 from the ultrasonic transducer 1 thru the couplant 3 to the surface of the object to be measured. The method of thickness inspection with ultrasonic waves requires the direction of path of propagation of the sound pulses be perpendicular to the surface of the area to be measured, and since the obstruction 20 obscures the surface and the transducer is physically too large to fit between the overhang and the surface, this surface cannot be ultrasonically inspected with traditional methods.

Figure 1B:
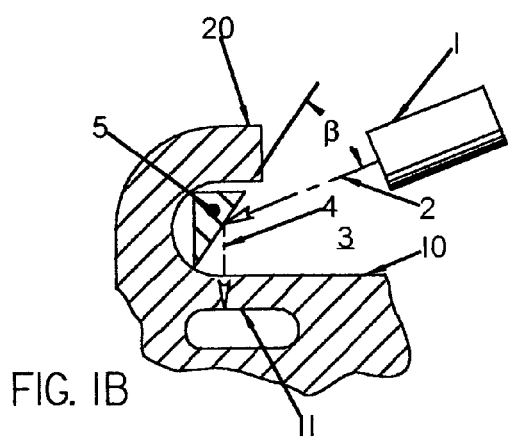
FIG. 1B is the same inspection represented in FIG. 1A using a reflector.

FIG. 1B shows the same object as in FIG. 1A, with the same surface being inspected ultrasonically with the use of a reflector. The sound waves leave the transducer 1, travel through the coupling fluid 3 along the path 2, and strike the reflector 5 located under the obstruction 20. Since the angle of incidence $\beta$ between the path of the sound and the surface of the reflector is less than the critical angle of refraction for the material of the reflector, the sound reflects from the surface and continues along path 4, until it strikes the surface of the object 10. A portion of the sound pulse is reflected from this surface, returns along the path and is detected by the transducer. The remaining sound energy enters the object, continues along the same path until it reaches the back surface of the object 11 where it is reflected and returns along the same path to the transducer where it is detected. The electronics associated with the transducer translate the time delay between the two pulses as a thickness.

Figure 2A:
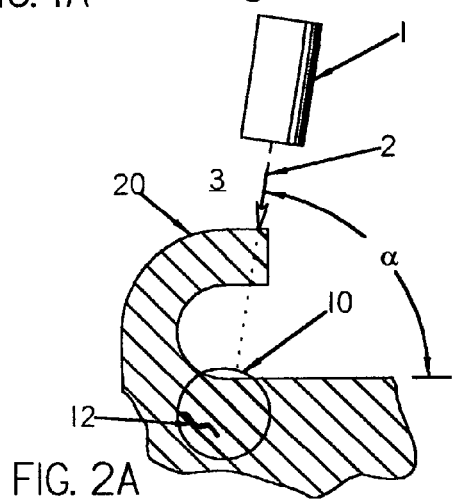
FIG. 2A is a side view demonstrating an attempt to inspect an area for a discontinuity inside a restricted space using a transducer.

FIG. 2A shows a cross sectional side view of an attempt to detect a discontinuity 12 in the material of an area 10 by transmitting an ultrasonic pulse from the ultrasonic transducer 1 along path 2 thru the couplant 3 to the surface of the area to be inspected. The method of discontinuity inspection with ultrasonic waves requires the angle $\alpha$ of path of propagation of the sound pulses, to be not perpendicular to the surface of the area to be measured, but be greater than the critical angle of refraction for that material, and since the obstruction 20 obscures the surface and the transducer is physically too large to fit between the obstruction and the surface, this area cannot be ultrasonically inspected with traditional methods.

Figure 2B:
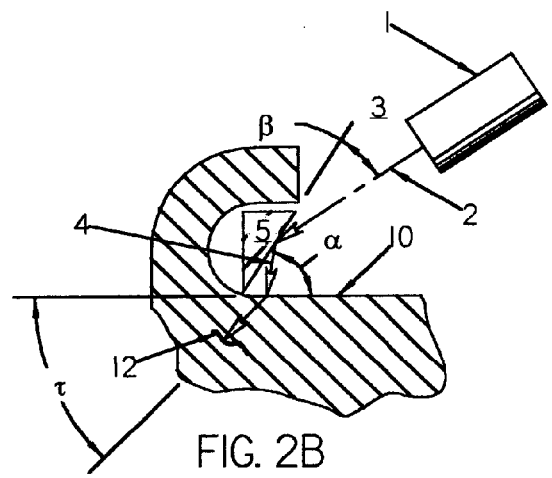
FIG. 2B is the same inspection represented in FIG. 2A using a reflector.

FIG. 2B shows the same object as in FIG. 2A, with the same surface being inspected ultrasonically with the use of a reflector. The sound waves leave the transducer 1, travel through the coupling fluid 3 along the path 2, and strike the reflector 5. Since the angle of incidence $\beta$ between the path of the sound and the surface of the reflector is less than the critical angle of refraction for the material of the reflector, the sound reflects from the surface and continues along path 4, until it strikes the surface of the object 10. The angle of incidence $\alpha$ between the sound pulse and the surface of the material is such that the majority of the energy of the sound pulse enters the material. The angle of propagation $\tau$ of the sound in the material is determined by the angle of incidence α and the refractive characteristics of the material and propagates through the material until it strikes the discontinuity 12. The sound pulse is then reflected back along the same path and returns to the transducer where it is detected. The electronics associated with the transducer translate the reflected sound and interpret it as a discontinuity.

Figure 3A:
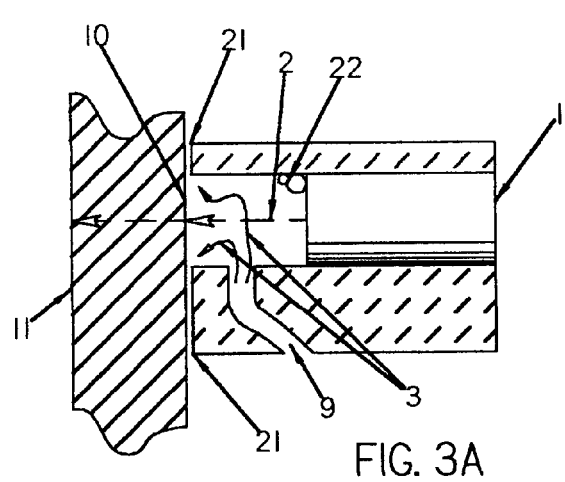
FIG. 3A is a side view demonstrating a transducer inspecting a vertical surface for thickness with air trapped in the couplant path.

Air, or any other gas can be trapped in the path from a transducer to the object to be inspected, and will attenuate the sound pulse which can make the measurement difficult or impossible. FIG. 3A shows a cross sectional side view of a measurement of the thickness of an object by transmitting an ultrasonic pulse from the ultrasonic transducer 1 along path 2 to the surface 10 and on to the far wall 11. The area between the transducer and the surface of the material to be measured is continuously replenished through a port 9 with the coupling fluid 3 which escapes through the gaps 21 between the transducer housing and the object. Entrained air 22 can be trapped in the path from the transducer to the object which will attenuate the sound pulse which can make the measurement difficult or impossible.

Figure 3B:
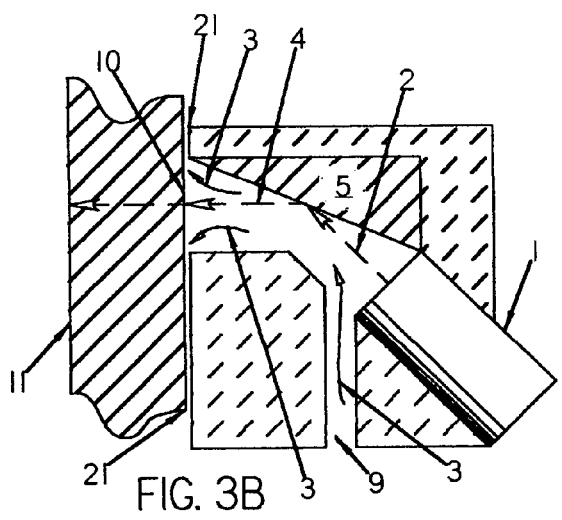
FIG. 3B is the same inspection represented in FIG. 3A using a reflector to eliminate the portion of the couplant path that can trap air.

FIG. 3B shows the same object as in FIG. 3A, with the same surface being inspected ultrasonically with the use of a reflector. The sound waves leave the transducer 1, travel through the coupling fluid 3 along the path 2, and strike the reflector 5. The sound reflects from the surface and continues along path 4, until it strikes the surface of the object 10. The area between the transducer and the surface of the material to be measured is continuously replenished through a port 9 with the coupling fluid 3 which escapes through the gaps 21 between the transducer housing and the object. A portion of the sound pulse is reflected from this surface, returns along the same path and is detected by the transducer. The remaining sound energy enters the object, continues in the same direction until it reaches the back wall of the object 11 where it is reflected and returns along the same path to the transducer where it is detected. The electronics associated with the transducer translate the time delay between the two pulses as a thickness. The reflector provides a surface that, due to its angle with the horizontal, forces any entrapped air along the surface of the reflector and out through the gap 21 between the transducer housing and the object being inspected.

A significant amount of the sound pulse of an ultrasonic test can be reflected by various imperfections of the surface, minor internal discontinuities such as inclusions and material grain boundaries, turbulence in the coupling fluid and such and is reflected to the transducer where it is detected. This is commonly known as noise and can interfere with and sometimes overwhelm the electronics of the ultrasonic system, which can make the test either difficult or impossible to conduct. FIG. 4A shows an object with the surface being inspected ultrasonically. The sound waves leave the transducer 1, travel through the coupling fluid 3 along the path 2, until it strikes the surface of the object 10. The angle of incidence between the sound pulse and the surface of the material is such that the majority of the energy of the sound pulse enters the material and propagates through the material until it strikes the discontinuity 12 and the back surface 11. The sound pulse is then reflected back along the same path and returns to the transducer where it is detected. The electronics associated with the transducer translate the reflected sound and interpret it as a discontinuity. A significant amount of the sound pulse is reflected to the transducer as noise 6 and can interfere with and sometimes overwhelm the electronics of the ultrasonic system which can make the test either difficult or impossible to conduct.

FIG. 4B shows the same object as in 4A, with the same surface being inspected ultrasonically with the use of a reflector. The sound waves leave the transducer 1, travel through the coupling fluid 3 along the path 2, and strike the reflector 5. The sound reflects from the surface and continues along path 4, until it strikes the surface of the object 10. The angle of incidence between the sound pulse and the surface of the material is such that the majority of the energy of the sound pulse enters the material and propagates through the material until it strikes the discontinuity 12 and the back surface 11. The sound pulse is then reflected back along the same path and returns to the transducer where it is detected. The electronics associated with the transducer translate the reflected sound and interpret it as a discontinuity. As in the similar test without a reflector, a significant amount of the sound pulse is reflected as noise 6, but due to the angle of the reflector and the orientation of the transducer it passes the reflector and the transducer, and therefore is not detected and cannot interfere with the test.

FIG. 4C is an oscillograph with shows various echo pulse signals which are the reflected pulses that are returned from the surfaces of a wall being measured in the manner indicated by FIG. 4A, showing signal amplitude A as a function of time T. The peaks generated by the noise 6 detected by the transducer compete with and can obscure the peak representing the discontinuity 12, which is the object of the test. The peak 10 is the detected reflected pulse from the near surface of the object, and the peak 11 is the pulse returned from the far surface.

FIG. 4D is an oscillograph which shows various echo pulse signals which are the reflected pulses that are returned from the surfaces of a wall being measured in the manner indicated by FIG. 4B. The noise 6 detected by the transducer is displayed as peaks that are greatly reduced in amplitude by use of the reflector, which makes the peak representing the discontinuity 12 much easier to analyze. The peak 10 is the detected reflected pulse from the near surface of the object, and the peak 11 is the pulse returned from the far surface.

Reflectors can also be used to split the ultrasonic pulses to test for multiple properties simultaneously.

FIG. 5A is a cut away isometric view showing a transducer inspecting a curved surface for multiple discontinuities when the long axis of the discontinuities is parallel with the axis of the curve, known as a longitudinal flaw, using a reflector to split the sound pulses. The sound waves leave the transducer 1, travel through the coupling fluid 3 along the path 2, and strike the reflector 5. As demonstrated in FIG. 5B, which is a top view of the same configuration, the sound redirected by the reflector 5 continues along paths 4 so as to strike the surface of the object 10 at right angles to the axis of the curve. As demonstrated in FIG. 5C, an end view of the same configuration with the transducer not shown, the sound redirected by the reflector 5 continues along paths 4 so the angle of incidence between the direction of the sound pulses and the tangent 14 to the surface 10 of the object in the plane of the reflected sound is more than the critical angle, but not perpendicular. This angle is such that the majority of the energy of the sound pulse enters the material and propagates through the material until it strikes the discontinuities at the far wall 12 and at the near wall 13. The sound pulses are then reflected back along the same paths and return to the transducer where they are detected.

FIG. 5D is a corresponding oscillograph which shows various echo pulse signals which are the reflected pulses that are returned from the surface and discontinuities being measured in the manner indicated by FIGS. 5A, 5B and 5C, showing signal amplitude A as a function of time T. The peaks are the amplitudes detected by the transducer of the reflected signals, of the near wall 10, the far wall discontinuity 12 and the near wall discontinuity 13. Since the transducer is too large to fit into the cavity perpendicularly to the walls this test cannot be done with conventional techniques.

Figure 6A:
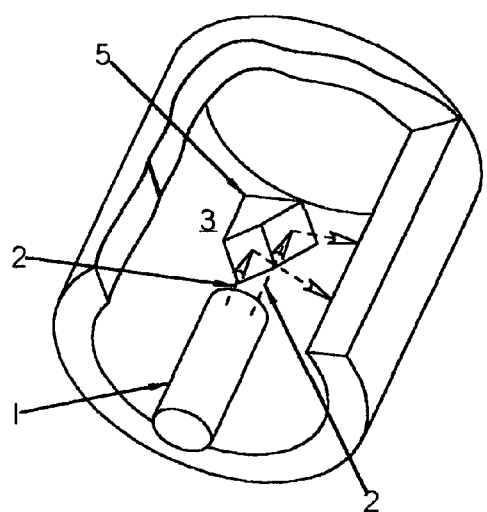
FIGS. 6A, 6B and 6C are respectively an isometric cut away view, and end view with the transducer not shown and a top view demonstrating a transducer inspecting a curved surface for multiple discontinuous perpendicular to the axis of the curve using a reflector to split the sound pulses.

FIG. 6A is a cut away isometric view showing a transducer inspecting a portion of a curved surface for multiple discontinuities when the long axis of the discontinuities is perpendicular to the axis of the curve, known as a transverse flaw, using a reflector to split the sound pulses. The sound waves leave the transducer 1, travel through the coupling fluid 3 along the paths 2, and strike the reflector 5. As demonstrated in FIG. 6B, which is an end view of the same configuration with the transducer not shown, the reflector 5 redirects the sound along path 4 by so as to strike the surface of the object 10 perpendicular to the axis of the curve. As demonstrated in FIG. 6C, a top view of the same configuration, the reflector 5 redirects the sound along paths 4 so the angle of incidence between the direction of the sound pulses and the surface of the object 10 in the plane of the reflected sound is more than the critical angle, but not perpendicular. This angle is such that the majority of the energy of the sound pulse enters the material and propagates through the material until it strikes the far wall 11, the discontinuities at the far wall 12 and at the discontinuities at the near wall 13. The sound pulses are then reflected back along the same paths and return to the transducer where they are detected.

Figure 6B:
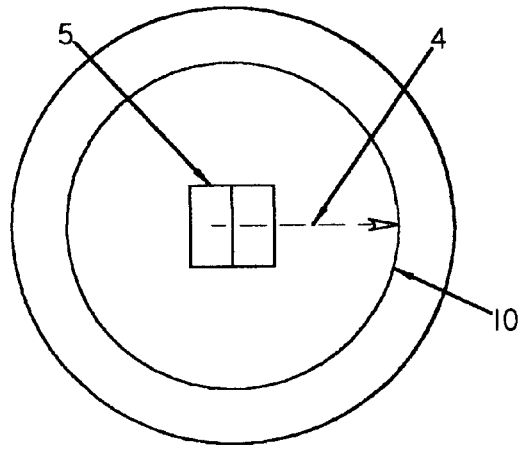
Figure 6C:
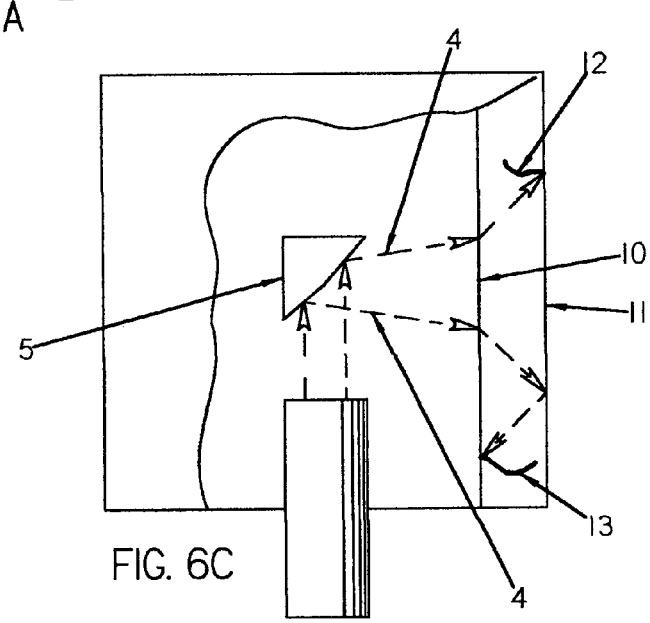
Figure 6D:
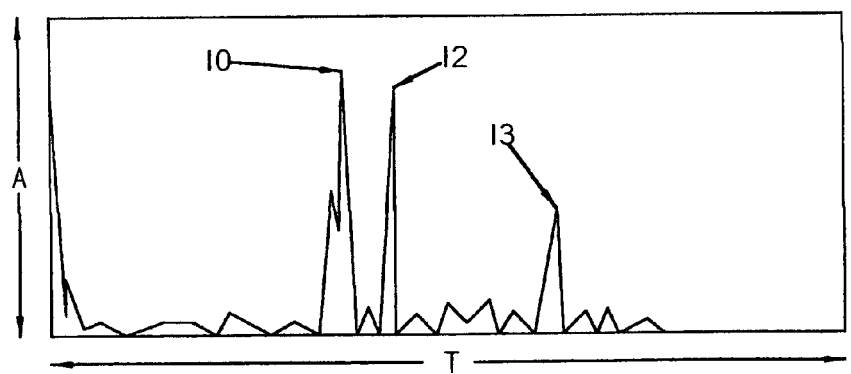
FIG. 6D is an oscillograph which shows various echo pulse signals which are the reflected pulses that are returned from the surfaces of a wall being measured in the manner indicated by FIG. 6A.

FIG. 6D is a corresponding oscillograph which shows various echo pulse signals which are the reflected pulses that are returned from the surface and discontinuities being measured in the manner indicated by FIGS. 6A, 6B and 6C, showing signal amplitude A as a function of time T. The peaks are the amplitudes detected by the transducer of the reflected signals, of the near wall 10, the far wall discontinuity 12 and the near wall discontinuity 13. Since the transducer is too large to fit into the cavity perpendicularly to the walls this test cannot be done with conventional techniques.

Figure 7A:
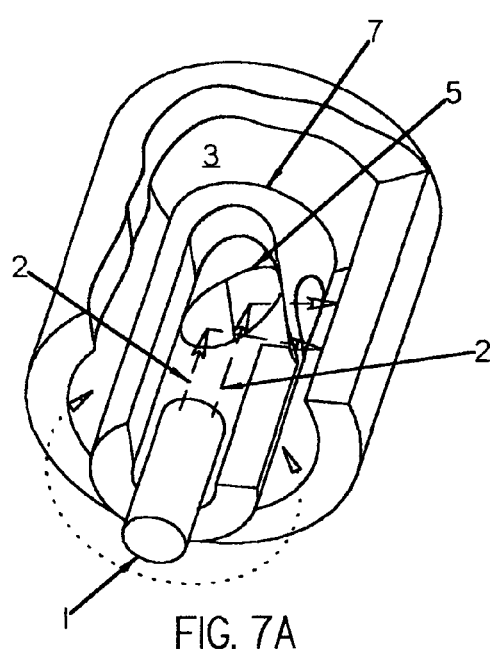
FIGS. 7A and 7B are respectively an isometric cut away view and a top view demonstrating a transducer inspecting a curved surface for multiple discontinuities perpendicular to the axis of the curve using a reflector mounted in a rotating housing to split the sound pulses.

FIG. 7A is a cut away isometric view showing a transducer inspecting a curved surface for multiple discontinuities for transverse flaws, using a reflector mounted in a rotating housing to split the sound pulses. The sound waves leave the transducer 1 which is fixed about its axis, travel through the coupling fluid 3 along the paths 2, and strike the reflector 5 which is permanently mounted to the housing 7. As demonstrated in FIG. 7B, a top view of the same configuration, the sound is redirected by the reflector 5 along paths 4 through a gap in the housing 7 to the surface of the object 10. The angle of incidence between the path of the sound pulses 4 and the surface of the object 10 in the plane of the reflected sound is more than the critical angle, but not perpendicular. This angle is such that the majority of the energy of the sound pulse enters the material and propagates through the material until it strikes the far wall 11, the discontinuities at the far wall 12 and at the discontinuities at the near wall 13. The sound pulses are then reflected back along the same paths and return to the transducer where they are detected. The transducer is fixed about its central axis so it cannot rotate. The housing assembly is mounted to the transducer with the reflector at a fixed distance from the transducer, but is free to rotate about it. As the housing rotates, the reflected pulses sweep a 360° path around the surface of the object. The transducer can then be moved along the surface along its central axis, which moves the housing and reflector with it, allowing for a full inspection of the entire volume over which the transducer and housing assembly are moved, in multiple signal directions simultaneously.

Figure 7B:
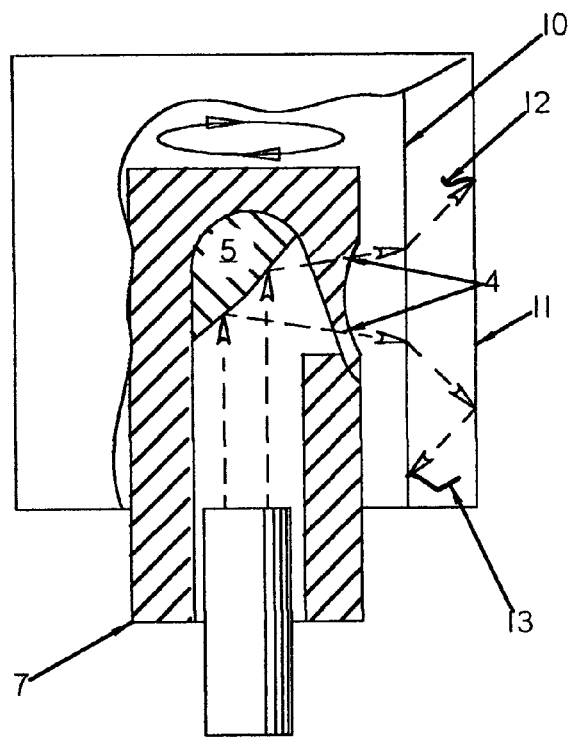
Figure 7C:
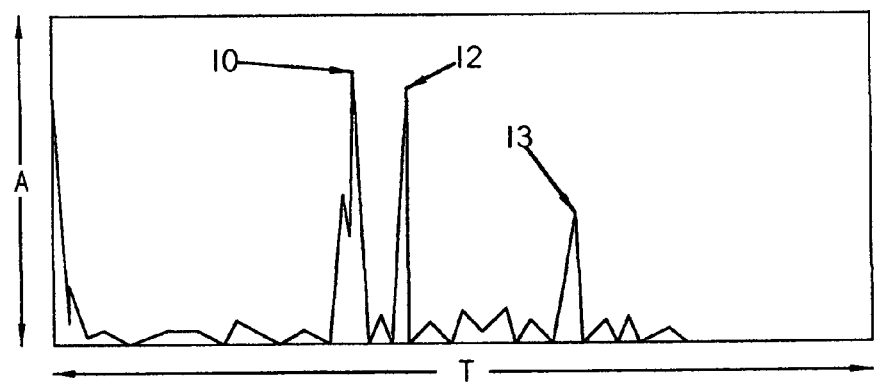
FIG. 7C is an oscillograph which shows various echo pulse signals which are the reflected pulses that are returned from the surfaces of a wall being measured in the manner indicated by FIG. 7A.

FIG. 7C is a corresponding oscillograph which shows various echo pulse signals which are the reflected pulses that are returned from the surface and discontinuities being measured in the manner indicated by FIGS. 7A and 7B, showing signal amplitude A as a function of time T. The peaks are the amplitudes detected by the transducer of the reflected signals, of the near wall 10, the far wall discontinuity 12 and the near wheel discontinuity 13. Since the transducer is too large to fit into the cavity perpendicularly to the walls, and multiple transducers would be required to scan the full surface this test cannot be done with conventional techniques.

What is claimed is:

1. In a pulse echo ultrasonic system for measuring properties of objects, the improvement comprising in combination,
   a means for generating a single directed ultrasonic pulse,
   a means for reflecting said pulse in a predetermined direction,
   a means of detecting pulses modified by properties of objects and evaluating them as per the property or properties being investigated,
   said direction being appropriate to permit the sound energy to impinge on the object of interest at the angle of incidence required for the inspection of the property or properties to be evaluated,
   said reflecting means being able to be located in areas inaccessible to said pulse generating device, or devices to redirect the pulses by refraction.

2. In a pulse echo ultrasonic system for measuring properties of objects, the improvement comprising in combination,
   a means for generating a single directed ultrasonic pulse,
   a means for reflecting said pulse in a predetermined direction,
   a means of detecting pulses modified by properties of objects and evaluating them as per the property or properties being investigated,
   said reflecting means being at an angle to said source so that entrained gas will be purged from the area between said source and the object to be investigated.

3. In a pulse echo ultrasonic system for measuring properties of objects, the improvement comprising in combination,
   a means for generating a single directed ultrasonic pulse,
   a means for splitting said single pulse into multiple pulses,
   a means of detecting pulses modified by properties of objects and evaluating them as per the property being investigated,
   said splitting means being comprised of multiple reflective surfaces,
   each said reflecting surface redirecting a portion of said original pulse at an angle of incidence relative to the surface of said object that will allow said portion of said pulse to impinge on said property to be evaluated,
   the angle of said reflecting surfaces being such that spurious or unwanted portions of the reflected pulse are not returned to the generating device.

4. In a pulse echo ultrasonic system for measuring properties of objects according to claim 3, wherein said improvement further comprises,
   said pulse generating means is stationary about its longitudinal axis,
   said splitting means is mounted in a housing,
   said housing rotates about the longitudinal axis of said pulse generating means to permit said object to be inspected for said properties in a 360° continuous sweep,
   said housing and said pulse generator can be moved along the surface of the test piece in tandem to inspect the entire volume of said object.

\* \* \* \* \*